US010678876B1

(12) United States Patent
Young et al.

(10) Patent No.: US 10,678,876 B1
(45) Date of Patent: Jun. 9, 2020

(54) COMPUTING SYSTEM FOR PRESENTING SUPPLEMENTAL CONTENT IN CONTEXT

(71) Applicant: Allscripts Software, LLC, Raleigh, NC (US)

(72) Inventors: Ohad Young, Hod Hasharon (IL); Alon Moshe Sabban, Rishon Le-Zion (IL); Mary Sumner Johnson, Raleigh, NC (US); Alisha Marie Belk, Raleigh, NC (US); Ross Carlyle Teague, Cary, CA (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 225 days.

(21) Appl. No.: 15/361,788

(22) Filed: Nov. 28, 2016

Related U.S. Application Data

(60) Provisional application No. 62/300,712, filed on Feb. 26, 2016.

(51) Int. Cl.
*G06F 16/9535* (2019.01)
*H04L 29/08* (2006.01)
*G06F 9/54* (2006.01)
*G16H 10/60* (2018.01)

(52) U.S. Cl.
CPC .......... *G06F 16/9535* (2019.01); *G06F 9/546* (2013.01); *G16H 10/60* (2018.01); *H04L 67/02* (2013.01)

(58) Field of Classification Search
CPC ...... G06F 3/048; G06F 16/9535; G06F 9/546; G16H 10/60; H04L 67/02
See application file for complete search history.

(56) References Cited

U.S. PATENT DOCUMENTS

| | | | |
|---|---|---|---|
| 8,949,427 B2 | 2/2015 | Dubbels et al. | |
| 9,727,348 B2* | 8/2017 | Chen | G06F 9/453 |
| 2003/0023717 A1* | 1/2003 | Lister | H04L 29/06 709/224 |
| 2009/0177495 A1 | 7/2009 | Abousy et al. | |
| 2011/0288877 A1 | 11/2011 | Ofek et al. | |
| 2012/0102560 A1* | 4/2012 | Arms | G06F 21/41 726/8 |
| 2012/0215560 A1 | 8/2012 | Ofek et al. | |
| 2012/0221535 A1 | 8/2012 | Dubbels et al. | |
| 2013/0218596 A1 | 8/2013 | Gome et al. | |
| 2014/0088988 A1* | 3/2014 | Fairbrothers | G06F 19/325 705/2 |
| 2014/0188516 A1* | 7/2014 | Kamen | G06F 19/3406 705/3 |
| 2014/0350954 A1 | 11/2014 | Ellis et al. | |
| 2015/0025911 A1 | 1/2015 | Altebrando et al. | |
| 2016/0054897 A1* | 2/2016 | Holmes | G06F 3/0481 715/740 |
| 2017/0091388 A1* | 3/2017 | Zolla | G06F 19/322 |

* cited by examiner

*Primary Examiner* — Albert M Phillips, III
(74) *Attorney, Agent, or Firm* — Medley, Behrens & Lewis, LLC

(57) ABSTRACT

Described herein are various technologies pertaining to displaying contextually relevant supplemental content retrieved from population data concurrently with data presented to a healthcare worker in a graphical user interface of an electronic health record application (EHR). Also described herein are graphical user interface features pertaining to concurrent display of a graphical user interface of the EHR and a graphical user interface of a supplement application.

20 Claims, 10 Drawing Sheets

COMPUTING SYSTEM FOR PRESENTING SUPPLEMENTAL CONTENT IN CONTEXT

RELATED APPLICATION

This application claims priority to U.S. Provisional Patent Application No. 62/300,712, filed on Feb. 26, 2016, and entitled "COMPUTING SYSTEM FOR PRESENTING SUPPLEMENTAL CONTENT IN CONTEXT", the entirety of which is incorporated herein by reference.

BACKGROUND

Electronic health record applications (EHRs) are robust applications that are utilized in medical facilities across a variety aspects of a medical practice. For example, and not by way of limitation, an EHR can include functionality related to patient intake, billing, updating medical records, prescribing medication, tracking care over time, and so forth. Computer-executable applications have been developed to supplement EHRs, wherein such supplement applications cannot be considered EHRs themselves (e.g., the supplement applications do not provide the breadth of features of EHRs, fail to meet regulatory requirements imposed on EHRs by governmental bodies, etc.). A supplement application can, for example, provide data about a patient that supplements the data about the patient in the EHR. Conventionally, these supplement applications are tightly integrated with EHRs. More specifically, conventionally, for an EHR to interact with a supplement application, the EHR must support certain integration standards, such as HL7 CCOW. Many EHRs (particularly legacy EHRs), however, do not support these integration standards, rendering the supplement applications inoperable with the EHRs (even though a supplement application can provide valuable information to a healthcare worker that is using an EHR that is incompatible with the supplement application).

SUMMARY

The following is a brief summary of subject matter that is described in greater detail herein. This summary is not intended to be limiting as to the scope of the claims.

Described herein are various technologies pertaining to computer-executable applications that are well-suited for use in a healthcare environment. More specifically, described herein are various technologies pertaining to a computer system, wherein a computer-executable supplement application can receive data from an EHR, and where the supplement application is configured to provide a healthcare worker that uses the EHR with contextually relevant information about a patient and/or population of patients. In an exemplary embodiment, the EHR does not support an integration standard, such as HL7 CCOW. The EHR, however, may be configurable to include a trigger, wherein in response to the trigger being activated, the EHR issues an application programming interface (API) call, wherein the API call can include data that is to be provided to a supplement application. Further, in the event where the supplement application is not currently being executed, the API call can cause the supplement application to be launched. The data included in the API call can include context data, where the context data comprises, for example, data that is indicative of an identity of a patient whose record is being viewed via the EHR, data that is indicative of an identity of a healthcare worker who is viewing or entering data about the patient via the EHR, etc.

The supplement application receives the context data included in the API call. For instance, the API call can be an HTTP/s request, where the context data is included in the HTTP/s request. The supplement application, immediately responsive to receiving the context data, constructs a query based upon the context data. The supplement application then executes a search over population data based upon the query, wherein the population data includes data retrieved from multiple sources. Such sources may include, but are not limited to, other EHRs, web pages from the World Wide Web, health care exchanges, etc. The supplement application then displays the retrieved data in a GUI of the supplement application, where the GUI of the supplement application is displayed concurrently with the GUI of the EHR, such that data relevant to the current context of the EHR (from the supplement application) is displayed concurrently with data presented by way of the EHR. In other words, the supplement application displays supplemental data that is relevant to the current context of the EHR, thereby presenting the healthcare worker with data that is relevant to what is being presented to the healthcare worker in the GUI of the EHR.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
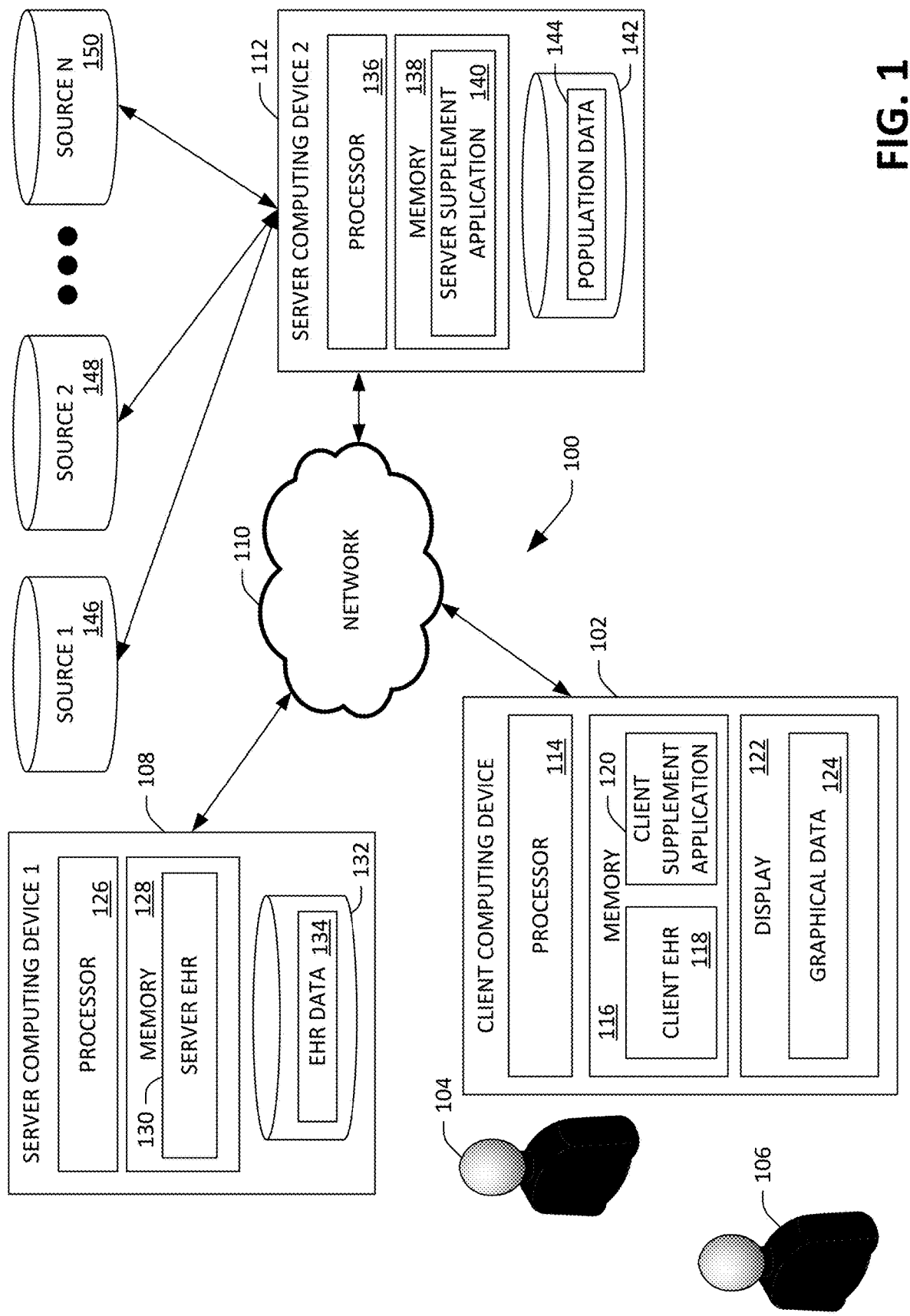
FIG. 1 is a functional block diagram of an exemplary system that facilitates presentment of supplemental data to a user of an EHR.

Various technologies pertaining to a supplement application that is configured to present contextually relevant data to a healthcare worker are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Generally, the features described herein pertain to technologies for providing contextual data from an EHR application to a supplement application, wherein a supplement application is one that is configured to present data to an end user that supplements what is being displayed to the end user by way of the EHR. Thus, for example, if the EHR is presenting information about a patient to an end user (e.g., such as a patient record), the EHR can be configured to provide a supplement application with data that is indicative of an identity of the end user. The supplement application may then be configured to present population data to the end user simultaneously with data that is presented to the end user by way of the EHR, wherein the population data pertains to the patient, and further where the population data is collected from data sources other than the EHR. Furthermore, as will be described in greater detail below, the EHR can be configured to provide the contextual data to the supplement application even when the EHR does not support an integration standard, such as HL7 CCOW.

Generally, an EHR is a distributed application that includes a client EHR executing on a client computing device and a server EHR executing on a server computing device. The client EHR, briefly, is configured to display data to a healthcare worker and receive input from the healthcare worker, while the server EHR is configured to acquire data based upon information received the client EHR and transmit information to the client EHR for presentment by way of the client EHR. Similarly, a supplement application is a distributed application that includes a client supplement application and a server supplement application. The client supplement application is configured to present data to an end user and receive input from the end user, while the server supplement application is configured to perform backend processing based upon data received from the client EHR.

Now referring to FIG. 1, an exemplary system 100 that facilitates presenting contextually-relevant supplemental data simultaneously with EHR data is illustrated. The system 100 includes a client computing device 102 that is operated by a healthcare worker 104 (e.g., a clinician, a billing specialist, etc.). The healthcare worker 104 may be utilizing the client computing device 102 in connection with providing care to a patient 106. While the patient 106 is shown as being in close proximity to the healthcare worker 104, it is to be understood that the healthcare worker 104 may be providing care to the patient 106 remotely. The client computing device 102 operated by the healthcare worker 104 may be any suitable type of client computing device, including a desktop computing device, a laptop computing device, a mobile telephone, a tablet computing device, a wearable computing device, or the like.

The system 100 further includes a first server computing device 108 that is in communication with the client computing device 102 by way of a suitable network 110, such as the Internet, an intranet, or the like. The system 100 further includes a second server computing device 112 that is in communication with the client computing device 102 by way of the network 110. While the system 100 is illustrated as including two server computing devices 108 and 112, it is to be understood that the system 100 may include a single server computing device that performs operations described below as being performed by the two server computing devices 108 and 112 separately. Further, while the client computing device 102 is depicted as being in communication with the server computing devices 108 and 112 by way of the network 110, it is to be understood that the client computing device 102 may be in communication with the server computing devices 108 and 112 over different networks. Further, the first server computing device 108 can be an enterprise device, whose operation is controlled by a healthcare enterprise. In another example, the first server computing device 108 can be a cloud-based computing device, where maintenance and operation of the first server computing device 108 is handled by a company that provides an EHR for use by a healthcare enterprise. Typically, the second server computing device 112 is a cloud-based computing device, where maintenance and operation of the second server computing device 112 is under the control of an entity that is separate from the healthcare enterprise.

The client computing device 102 includes a processor 114 and memory 116. The memory 116 stores instructions that are executed by the processor 114. More specifically, the memory 116 includes a client EHR 118 and a client supplement application 120. As will be described in greater detail herein, the client supplement application 120 is configured to cause (contextually relevant) data to be displayed that is supplemental to data being presented to the healthcare worker 104 by way of the client EHR 118. The client computing device 102 further comprises a display 122, which is configured to present graphical data 124 to the healthcare worker 104. The graphical data 124 may include data presented by way of the client EHR 118 and data presented by way of the client supplement application 120. While the display 122 is depicted as being integral to the client computing device 102, it is to be understood that the display 122 may be externally coupled to the client computing device 102 or may be a projected display.

The first server computing device 108 comprises a processor 126 and memory 128 that stores instructions that are executed by the processor 126. As shown in FIG. 1, the memory 128 includes a server EHR 130. The first server computing device 108 further includes a data store 132 that comprises EHR data 134. In operation, the healthcare worker 104 can interact with the client EHR 118 executing on the client computing device 102. This interaction causes the client EHR 118 to transmit data to the server EHR 130 executing on the first server computing device 108. Content of the data transmitted to the server EHR 130 can include, for instance, data that identifies the healthcare worker 104 and data that identifies the patient 106, amongst other data. Responsive to receipt of such data, the server EHR 130 can construct a query based upon the data and search over the EHR data 134 in the data store 132 based upon the query, thereby obtaining search results. The EHR data 134 can include any suitable data that is used in connection with provision of care to the patient 106, including an electronic patient record for the patient 106. The server EHR 130 then causes the first server computing device 108 to transmit the search results to the client computing device 102, whereupon the search results are provided to the client EHR 118. The client EHR 118 subsequently causes at least a portion of the search results to be presented in the graphical data 124 on the display 122 of the client computing device 102.

In a more specific example, the healthcare worker 104, through utilization of a human machine interface (HMI), can interact with the client EHR 118 by providing input pertaining to the patient 106. The client EHR 118 transmits this information to the server EHR 130, which can construct a query based upon the data and search over the EHR data 134 using the query. The server EHR 130 can then return corresponding search results to the client EHR 118. The client EHR 118 causes at least a portion of the search results (e.g., a portion of an electronic medical record (EMR) of the patient 106) to be displayed on the display 122 (e.g., as part of the graphical data 124).

The second server computing device 112 includes a processor 136 and memory 138 that stores instructions that are executed by the processor 136. As shown, the memory 138 includes a server supplement application 140. The second server computing device 112 further includes a data store 142 that comprises population data 144. The population data 144 may include data retrieved from multiple data sources 146-150 that are in network communication with the second server computing device 112. For example, the first source 146 may be a first EHR (other than the EHR used by the healthcare worker 104), the second source 148 may be a second EHR, and the nth source 150 may be include a web site. It can therefore be ascertained that the population data 144 can include population health data retrieved and aggregated from a myriad of different data sources, wherein at least some of the population data 144 pertains to the patient 106 and is not duplicative as to data about the patient 106 in the EHR data 134.

Operation of the client supplement application 120 and the server supplement application 140 is now described. The client supplement application 120 can receive input from the healthcare worker 104 directly or indirectly. For instance, the display 122 can present a GUI for the client supplement application 120, and the client supplement application 120 can receive input directly from the healthcare worker 104. In another example, the client EHR 118 can provide data to the client supplement application 120, wherein the data provided to the supplement application 120 by the client EHR 118 can be based upon interaction of the healthcare worker 104 with the client EHR 118. The client supplement application 120, in response to receiving data from either the healthcare worker 104 or the client EHR 118, causes the client computing device 102 to transmit data to the second server computing device 112 by way of the network 110. The server supplement application 140 receives the data, constructs a query based upon the data, and executes a search over the population data 144 in the data store 142 using the query, thereby generating search results. The server supplement application 140 then causes the server computing device 112 to transmit at least a portion of the search results to the client computing device 102 by way of the network 110, whereupon the search results are provided to the client supplement application 120. The client supplement application 120 causes at least a portion of the results to be displayed on the display 122 in the graphical data 124. As will be shown and described in greater detail herein, the client supplement application 120 can cause the search results to be presented concurrently with data presented by the client EHR 118, wherein the search results are contextually relevant to the data displayed by the client EHR 118.

Figure 2:
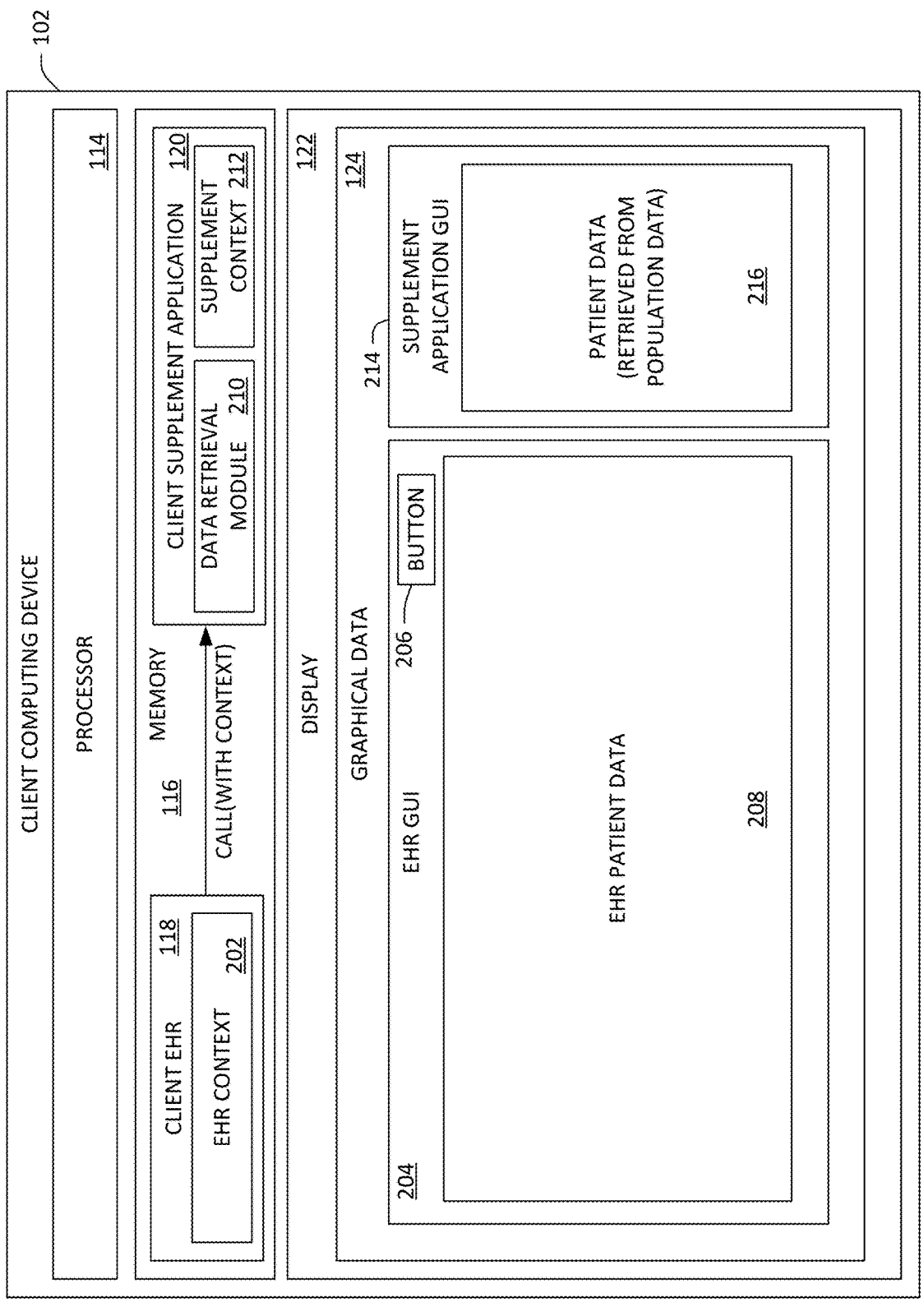
FIG. 2 depicts an exemplary client computing device.

With reference now to FIG. 2, a functional block diagram of the client computing device 102 is illustrated. As indicated previously, the client EHR 118 is loaded in the memory 116 and is executed by the processor 114. The client EHR 118 has an EHR context 202, where the EHR context 202 is indicative of a current state of the client EHR 118, including an identity of the healthcare worker 104 utilizing the client EHR 118, an identity of the patient 106 (e.g., when data about the patient is loaded into the client EHR 118), etc. The processor 114, when executing the client EHR 118, causes a client EHR GUI 204 to be included in the graphical data 124 on the display 122. In this example, the client EHR GUI 204 comprises EHR patient data (data about the patient 106). The client EHR GUI 204 further includes a button 206, wherein the button 206, when selected by the healthcare worker 104 (e.g., by way of a mouse pointer, voice command, interaction with a touch sensitive display, etc.), is configured to cause the EHR context 202 to be provided to the client supplement application 120. Further, when the client supplement application 120 is not being executed by the processor 114, the processor 114 can be configured to launch the client supplement application 120 responsive to the button 206 being selected. Moreover, the client supplement application 120 may be executed by the processor 114 in the background; the processor 114 can be configured to execute the client supplement application 120 in the foreground responsive to the button 206 being selected.

While the EHR GUI 204 is depicted here as including the button 206, it is to be understood that the EHR GUI 204 can include any suitable trigger that, when activated, causes the EHR context 202 to be provided to the client supplement application 120. Exemplary triggers include, but are not limited to, dropdown menu selections, page loads through use of navigation, etc. Further, the trigger may be voice-activation, wherein the client EHR 118 provides the EHR context 202 in response to receipt of a voice command. Thus, description of the EHR GUI 204 including the button 206 is exemplary, and it is to be understood that the client EHR 118 can be caused to provide the supplement application 120 with the EHR context 202 by way of any suitable trigger.

Additional detail pertaining to the client EHR 118 (and the server EHR 130) is now set forth. The EHR (client and server) may not support integration standards, such as HL7 CCOW; therefore, the supplement application (client and server) is unable to be tightly integrated with the EHR, as the EHR is unable to communicate directly to the supplement application. The EHR, however, allows for customization such that a widget (the button 206) is included in the EHR GUI 204, where the client EHR 118 generates an API call (e.g., an HTTP/s request) responsive to the button 206 being selected. Stated another way, when the healthcare worker 104 selects the button 206, the client EHR 118 outputs an API call (e.g., in the form of an HTTP/s request) that includes data based upon the EHR context 202. In a nonlimiting example, the API call can include context data, where the context data may include, but is not limited to including, the following information: data that is indicative of an identity of the patient 106 (e.g., a patient ID, which can be or include a patient assigning authority system and patient MRN, a full name of the patient 106, etc.), demographics about the patient 106 (e.g., gender, date of birth, zip code, etc.), data that is indicative of an identity of the healthcare worker 106, and/or the like. The data that is indicative of the identity of the healthcare worker 104 can be included in the API call as a single sign-on (SSO) based on an SAML token or an SSO that is based on an account of the healthcare worker 104 with the EHR, and/or the username of the healthcare worker 104 with the EHR.

The client supplement application 120, when executed by the processor 114 (in either the foregoing or the background), can monitor a port for API calls output by the client EHR 118, and can receive the context data responsive to detecting an API call. In another example, when the client supplement application 120 is not being executed by the processor 114, the processor 114 can launch the client supplement application 120 in response to the client EHR 118 outputting the API call. The client supplement application 120 receives the context data included in the API call. The client supplement application 120 comprises a data retrieval module 210 that receives the context data in the API call, and causes the client computing device 102 to transmit the context data the second server computing device 112 (FIG. 1). The server supplement application 140, as indicated previously, constructs a query based upon context data, and executes the query over the population data 144 to obtain search results. The server supplement application 140 then causes the second server computing device 112 to transmit at least a portion of the search results back to the client computing device 102 by way of the network 110. In another exemplary embodiment, rather than the server supplement application 140 constructing the query, the data retrieval module 210 of the client supplement application 120 can construct the query based upon the context data, and transmit the query to the second server computing device 112.

The search results received at the client computing device 102 can then be loaded into the client supplement application 120 as supplement context data 212. The processor 114, in response to the client supplement application 120 receiving the API call generated by the client EHR 118, causes a supplement application GUI 214 to be rendered on the display 122 as part of the graphical data 124. The supplement application GUI 214 includes patient data 216 (data in the search results retrieved from the population data 144 by the server supplement application 140). This patient data 216 is data that supplements the EHR patient data 208, such that the healthcare worker 104 can better service the patient 106. Moreover, since the query executed by the server supplement 140 can include or be based upon data that is indicative of the identity of the healthcare worker 104, the patient data 216 may include data that is relevant to the healthcare worker 104 (e.g., is relevant to a role of the healthcare worker 104 in a medical facility).

The example set forth above pertains to the situation where the client EHR 118 is displaying data about the patient 106. In the scenario where the client EHR context 202 is not patient-centric, the client supplement application 120 and/or the server supplement application 140 can construct a query that is based solely upon the identity of the healthcare worker 104. Thus, the client supplement application GUI 214 may present population health data rather than patient-centric data.

Figure 3:
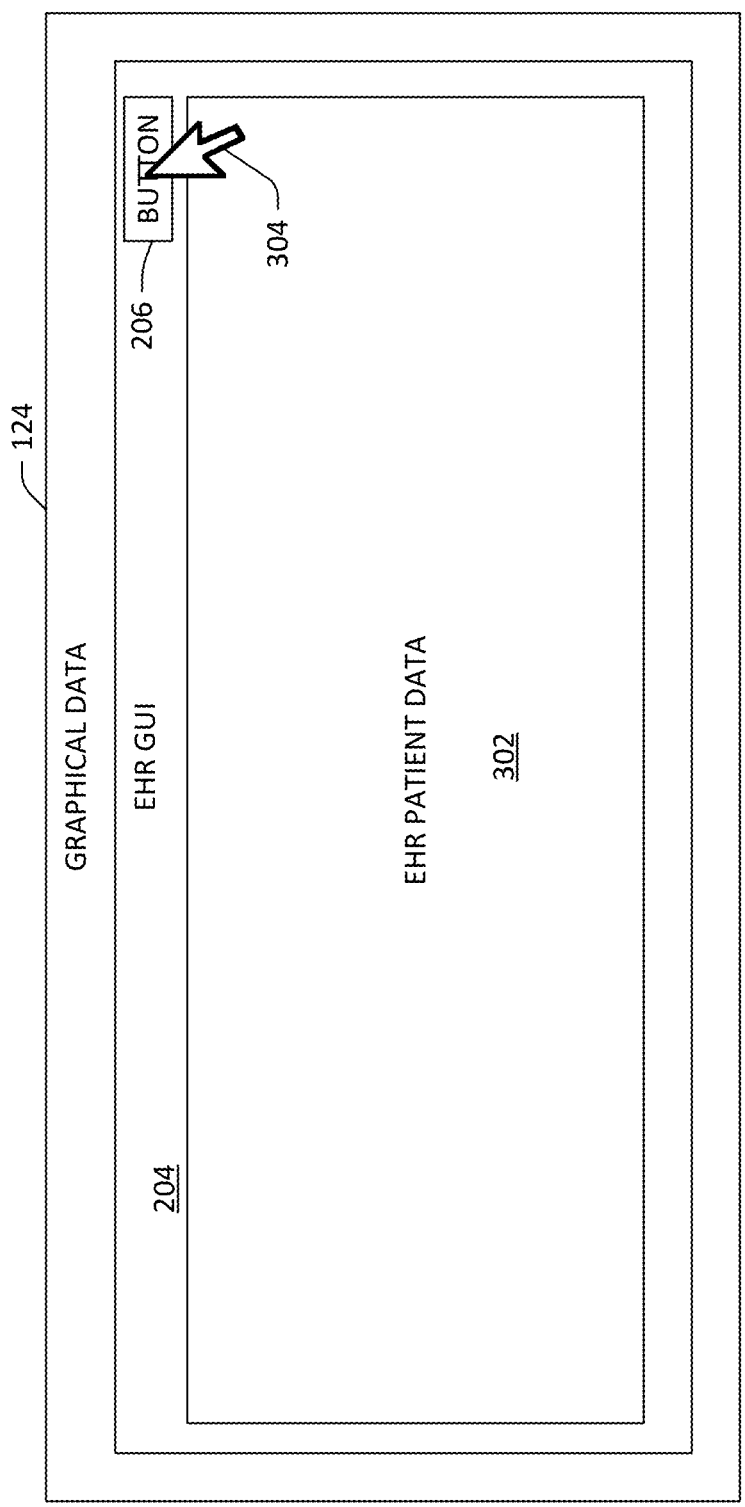
FIG. 3 is an exemplary graphical user interface of an EHR.

Turning now to FIG. 3, a depiction of the graphical data 124 prior to the supplement application GUI 214 being presented on the display 122 is illustrated. In this example, the graphical data 124 shown on the display 122 of the client computing device 102 includes the EHR GUI 204, which includes the button 206 and a field 302 for depicting the EHR patient data. In the example shown in FIG. 3, the healthcare worker 104 positions a cursor 304 over the button 206 and selects the button 206 through use of the cursor 304.

Figure 4:
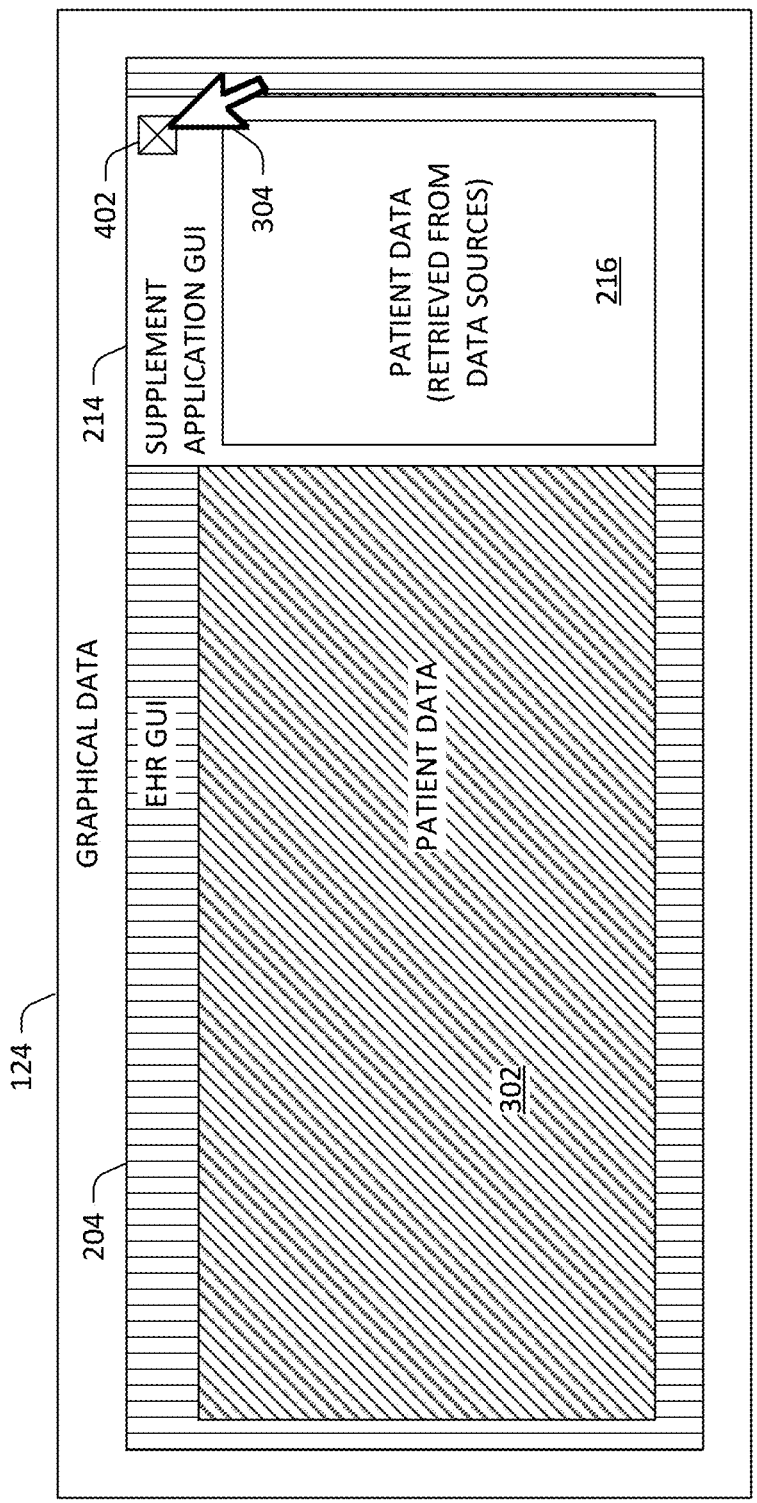
FIG. 4 depicts an exemplary supplement application GUI.

Now referring to FIG. 4, the graphical data 124 is depicted, in an exemplary embodiment, when the supplement application GUI 214 is included in the graphical data 124 concurrently with the EHR GUI 204. As noted previously, the EHR may not support integration standards; therefore, changes in the EHR context 202 may not be automatically communicated to the supplement application. Due to this lack of communication between the EHR and the supplement application, a potential problem may arise, where the healthcare worker 104 could change the EHR context 202 (e.g., cause the EHR GUI 204 to present data about one patient while the supplement application GUI 214 simultaneously presents data about another patient).

Various approaches are described herein to prevent such a situation from occurring. As shown in FIG. 4, when the processor 114 causes the supplement application GUI 214 to be shown on the display 122, the supplement application GUI 214 (which depicts the patient data 216) can be rendered such that at least a portion of the supplement application GUI 214 is a transparent or semi-transparent overlay on top of the EHR GUI 204, wherein the supplement application GUI 214 entirely overlays the EHR GUI 204. More specifically, the client supplement application 120 can receive information from the operating system of the client computing device 102 as to the boundaries of the EHR GUI 204 on the display 122. The client supplement application 120 may then generate its GUI 214 such that it entirely overlays the EHR GUI 204, thereby preventing the healthcare worker 104 from interacting with the client EHR 118 by way of the EHR GUI 204 (unless the supplement application GUI 214 is closed). As a portion of the overlay, however, is transparent or semi-transparent, the healthcare worker 104 can simultaneously review the patient data shown in the EHR GUI 204 and the patient data 216 presented in the supplement application GUI 214. When the healthcare worker 104 wishes to interact with the client EHR 118 by way of the EHR GUI 204, the healthcare worker 104 must close (or minimize) the supplement application GUI 214. As shown, the supplement application GUI 214 includes a button 402 that, went selected, causes the supplement application GUI 214 to be closed or minimized (and optionally causes the client supplement application 120 to close), thereby removing the supplement application GUI 214 from the graphical data 124, and placing the graphical data 124 in the state shown in FIG. 3. After the supplement application GUI 214 has been closed, the healthcare worker 104 is free to interact with the client EHR 118 by way of the EHR GUI 204.

Figure 5:
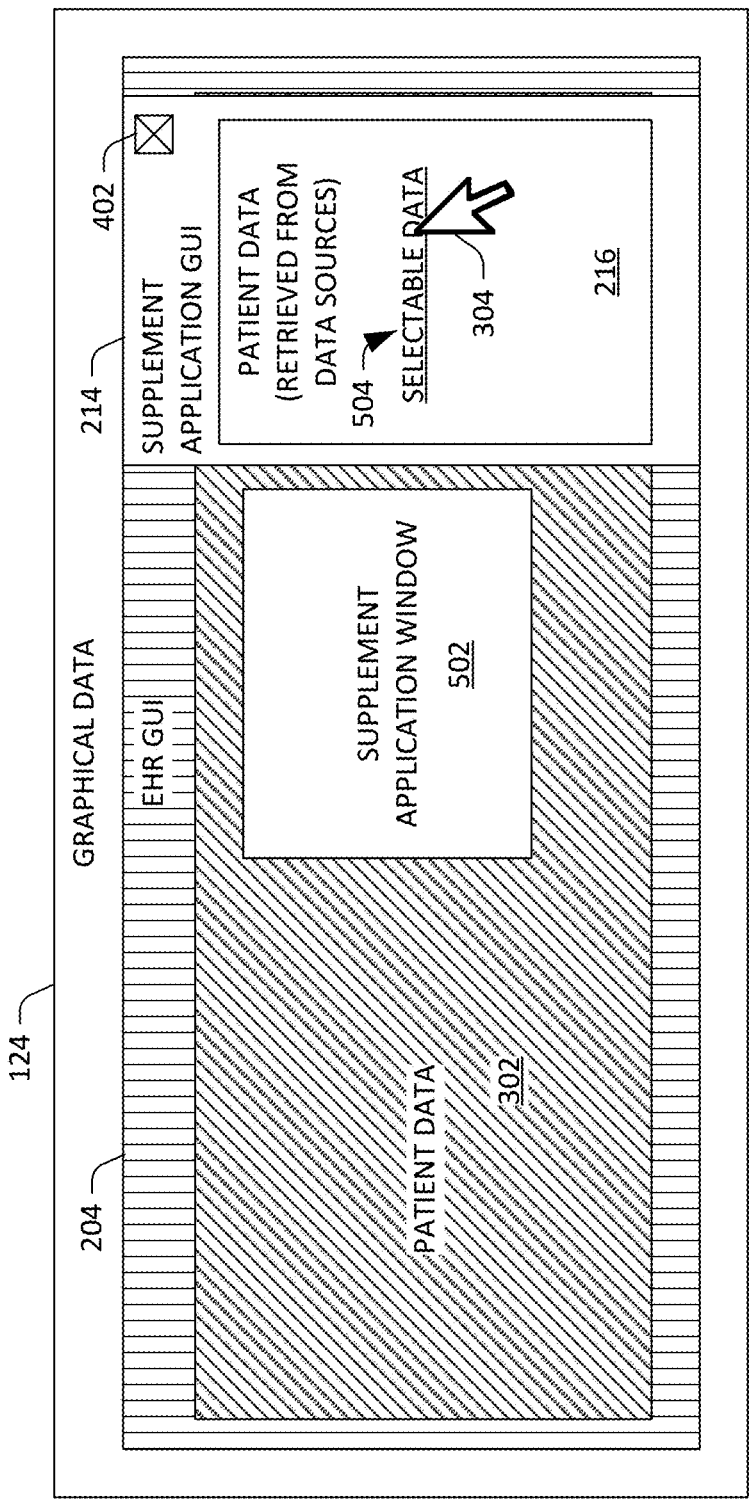
FIG. 5 depicts another exemplary supplement application GUI.

Now referring to FIG. 5, presentment of a window 502 in the graphical data 124 is depicted. In this example, the patient data 216 includes selectable data 504 (e.g., presented in the patient data 216 as a hyperlink). The cursor 304 can be used to select the selectable data 504, and responsive to the selectable data 504 being selected, the client supplement application 120 causes the supplement application window 502 to be opened and included in the graphical data 124 on the display 122. The supplement application window 502 may include data related to the selectable data 504 in the patient data 216. The exemplary graphical data 124 shown in FIG. 5 indicates that the healthcare worker 104 is able to interact with the client supplement application 120, since data generated or presented by such application 120 remains contextually relevant to the patient data presented by way of the client EHR 118. As indicated previously, however, in this embodiment, the healthcare worker 104 is unable to interact with the client EHR 118 unless and until the supplement application GUI 214 is closed or minimized.

Figure 6:
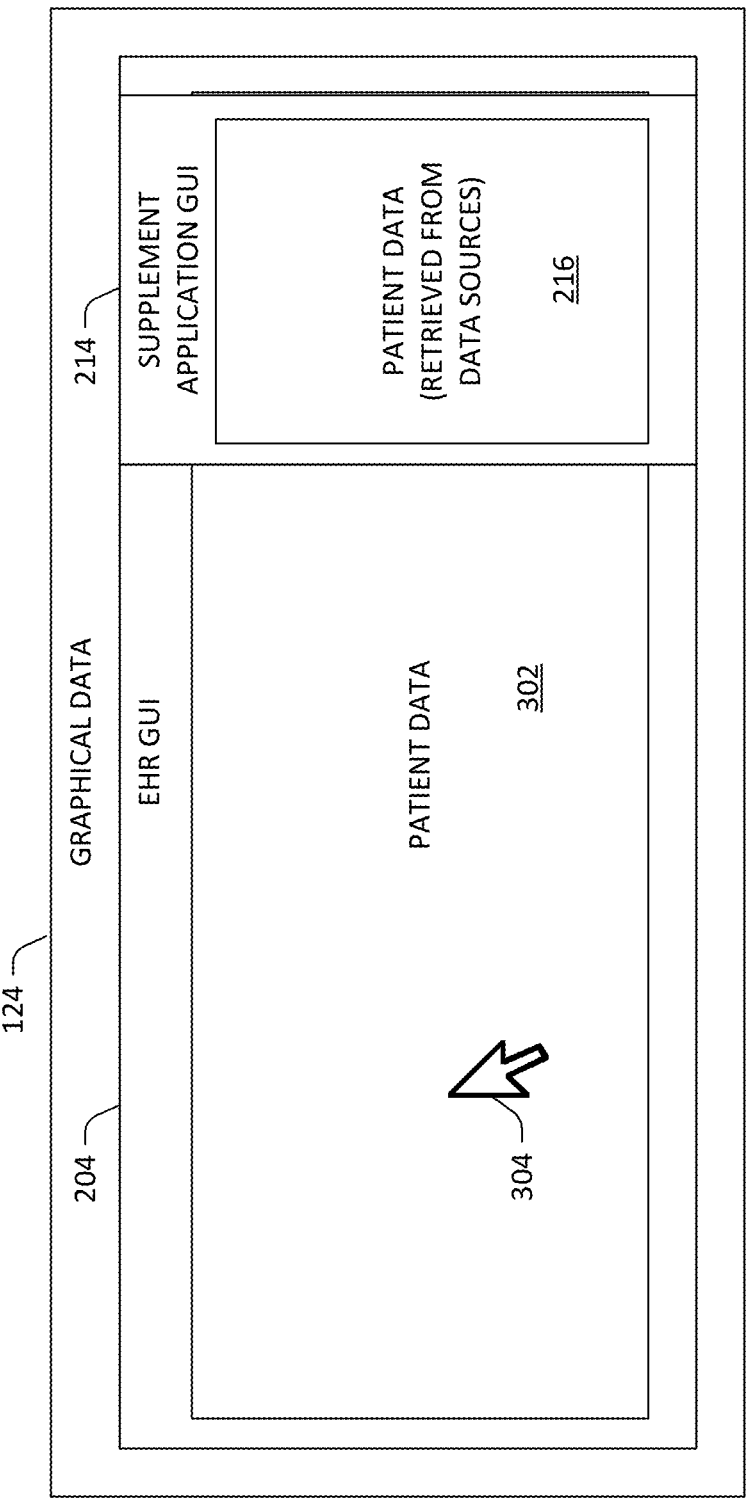
FIG. 6 illustrates yet another exemplary supplement application GUI.

Now referring to FIG. 6, another exemplary embodiment pertaining to simultaneous presentment of the EHR GUI 204 and the supplement application GUI 214 is illustrated. In this example, the processor 114 causes the supplement application GUI 214 to be presented responsive to the button 206 being selected. When the healthcare worker 104, however, attempts to interact with the client EHR 118 by way of the EHR GUI 204, the processor 114 is configured to immediately close the supplement application GUI 214. Therefore, for example, if the healthcare worker 104 selected a different patient in the EHR GUI 204, the supplement application GUI 214 is immediately closed, such that the supplement application GUI 214 is immediately removed from the graphical data 124. To cause the supplement application GUI 214 to be included in the graphical data 124 again, the button 206 must be re-selected (which will cause contextually relevant data to be presented in the supplement application GUI 214). This ensures that the patient data 216 presented in the supplement application GUI 214 is relevant to the patient data shown in the field 302 of the EHR GUI 204.

Figure 7:
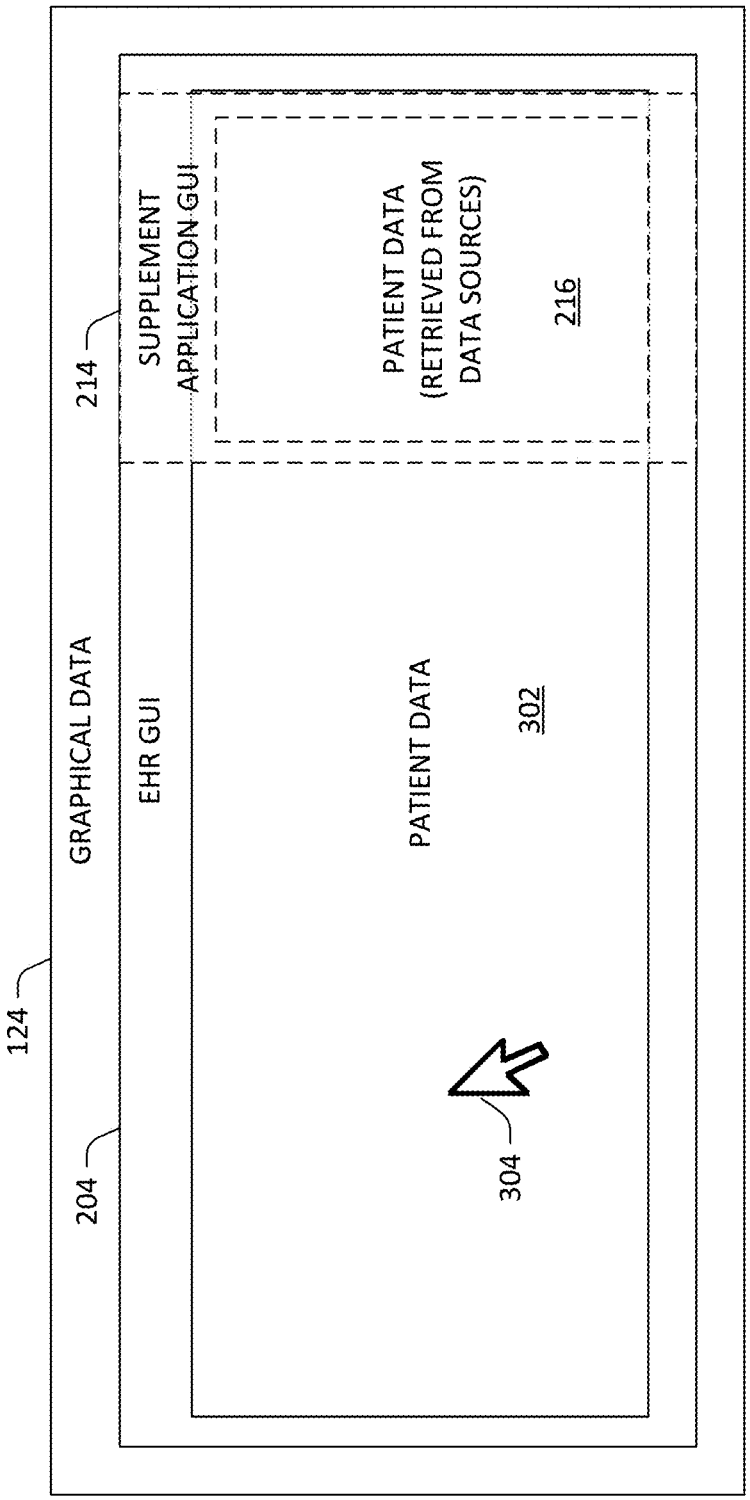
FIG. 7 illustrates a supplement application GUI being faded out.

Turning now to FIG. 7, yet another exemplary feature pertaining to simultaneous presentment of the EHR GUI 204 and the supplement application GUI 214 is illustrated. As with the previous example, the supplement application GUI 214 is presented responsive to the button 206 in the client EHR GUI 204 being selected. As shown by the dashed lines, the processor 114 causes the supplement application GUI 214 to "fade away" when the cursor 304 is positioned outside of the supplement application GUI 214. For instance, the supplement application GUI 214 may fade away after some threshold amount of time where the cursor 304 is not located over a region that corresponds to the supplement application GUI 214. This amount of time between when fade begins and when the supplement application GUI 214 is closed may be relatively short, to ensure that the healthcare worker 104 is not simultaneously looking at data about different patients when reviewing the graphical data 124.

Figure 8:
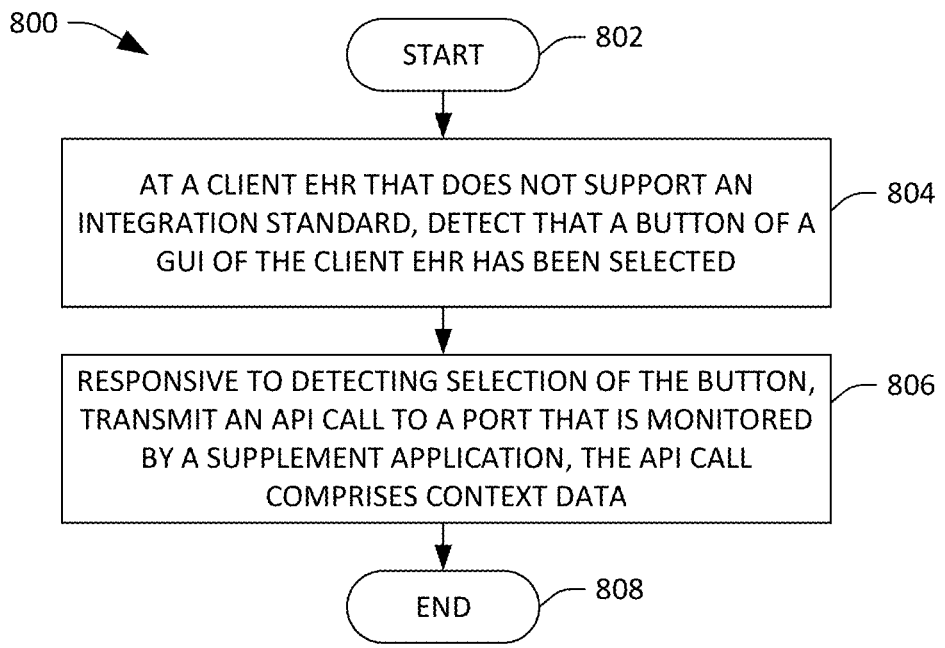
FIG. 8 is a flow diagram illustrating an exemplary methodology for generating and output an API call for receipt by a client supplement application.
Figure 9:
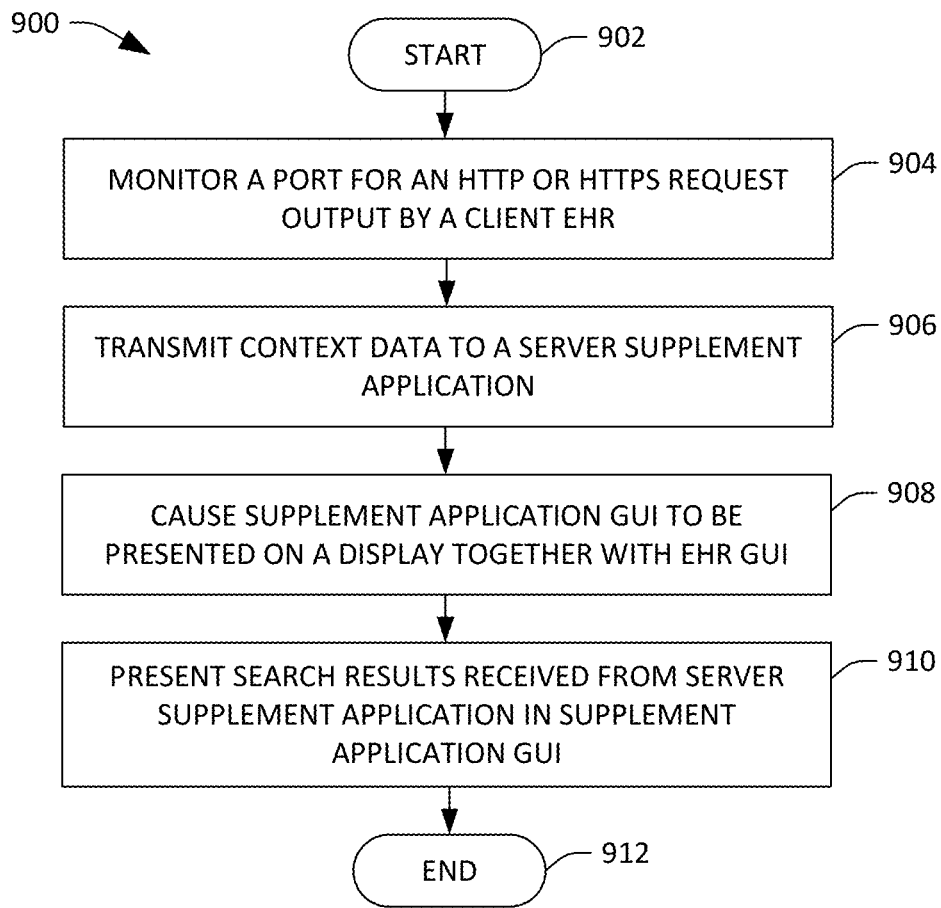
FIG. 9 is a flow diagram illustrating an exemplary methodology for presenting information that is contextually relevant to information being shown in a GUI of an EHR.

FIGS. 8-9 illustrate exemplary methodologies relating to presentment of contextually relevant content to a healthcare worker using an EHR. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring solely to FIG. 8, an exemplary methodology 800 that is performed by a client computing device that executes a client EHR is illustrated. The methodology 800 starts at 802, and at 804, it is detected that a button depicted on an EHR GUI has been selected by a healthcare worker, wherein the EHR GUI is for the client EHR. At 806, responsive to detecting that the button has been selected by the healthcare worker, an API call is generated, wherein the API call includes context data. The context data is indicative of a current state of the client EHR, and can include, but is not limited to including, an identifier for a patient whose information is being reviewed by way of the client EHR, an identifier for a healthcare worker who is using the EHR, demographic information about the patient, medication prescribed to the patient, geographic information pertaining to the patient, etc. As noted above, the API call can be in the form of an HTTP/s request. A client supplement application can monitor a port for HTTP/s requests, and can effectively "intercept" the HTTP/s request, thereby acquiring the context data without requiring the supplement application to be tightly integrated with the EHR. The methodology 800 completes at 808.

Referring now to FIG. 9, an exemplary methodology 900 that facilitates presenting information that is contextually relevant to data presented by way of an EHR to a healthcare worker is illustrated. The methodology 900 is performed at a client computing device that executes a client EHR application and a client supplement application, wherein the EHR application and the client supplement application are not tightly integrated. The methodology 900 starts at 902, and at 904, a port is monitored by the client supplement application for an HTTP/s request that is output by a client EHR. For instance, as described above, the client EHR can output the HTTP/s request responsive to a healthcare worker that is utilizing the client EHR selecting a button in the GUI of the EHR. The HTTP/s request includes context data, which has been described above. At 906, in response to receiving the HTTP/s request, the client supplement application causes the context data to be transmitted to a server computing device that executes a server supplement application. The server supplement application receives the context data and performs a search over population data that is maintained by the server supplement application. The server supplement application causes the server computing device to transmit search results to the client computing device, whereupon it is received by the client supplement application.

At 908, in response to detecting the HTTP/s request, a GUI for the supplement application is presented on a display of the client computing device together with the GUI of the EHR. At 910, the search results from the server supplement application are presented in the GUI for the supplement application. Thus, the GUI for the supplement application displays data that is contextually relevant to data presented in the GUI of the EHR. The methodology 900 completes at 912.

Figure 10:
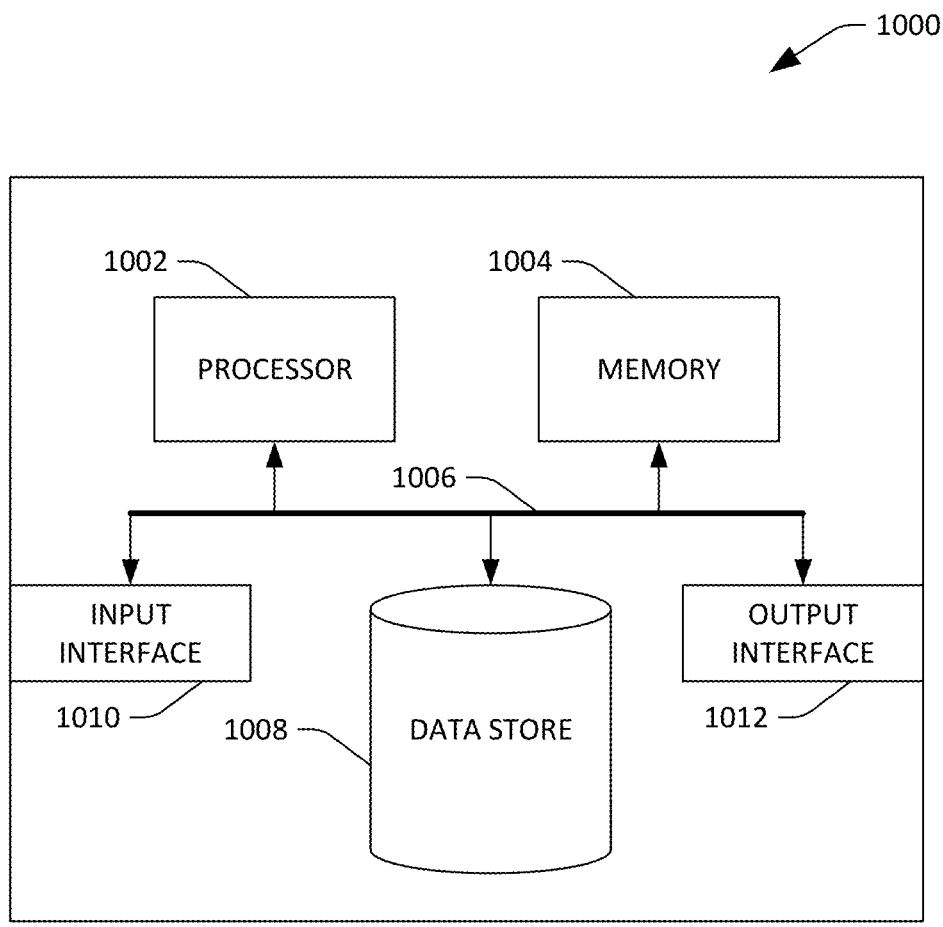
FIG. 10 is an exemplary computing system.

Referring now to FIG. 10, a high-level illustration of an exemplary computing device 1000 that can be used in accordance with the systems and methodologies disclosed herein is illustrated. For instance, the computing device 1000 may be used in a system that executes an EHR. By way of another example, the computing device 1000 can be used in a system that executes a supplement application. The computing device 1000 includes at least one processor 1002 that executes instructions that are stored in a memory 1004.

The instructions may be, for instance, instructions for implementing functionality described as being carried out by one or more components discussed above or instructions for implementing one or more of the methods described above. The processor 1002 may access the memory 1004 by way of a system bus 1006. In addition to storing executable instructions, the memory 1004 may also store patient-centric data, population data, etc.

The computing device 1000 additionally includes a data store 1008 that is accessible by the processor 1002 by way of the system bus 1006. The data store 1008 may include executable instructions, patient-centric data, population data, etc. The computing device 1000 also includes an input interface 1010 that allows external devices to communicate with the computing device 1000. For instance, the input interface 1010 may be used to receive instructions from an external computer device, from a user, etc. The computing device 1000 also includes an output interface 1012 that interfaces the computing device 1000 with one or more external devices. For example, the computing device 1000 may display text, images, etc. by way of the output interface 1012.

It is contemplated that the external devices that communicate with the computing device 1000 via the input interface 1010 and the output interface 1012 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1000 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1000 may be a distributed system. Thus, for instance, several devices may be in communication by way of a network connection and may collectively perform tasks described as being performed by the computing device 1000.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computing device comprising:
   at least one processor; and
   memory that stores instructions that, when executed by the at least one processor, cause the at least one processor to perform acts comprising:
   detecting an application programming interface (API) call generated by a client electronic health record application (EHR) that is being executed by the at least one processor to a server EHR that is executing on a first server computing device that is in network communication with the computing device, wherein the API call comprises context data that is indicative of content currently being displayed in a graphical user interface (GUI) of the client EHR, wherein the API call is transmitted to the server EHR;
   responsive to detecting the API call at the computing device, extracting the context data from the API call and transmitting the context data to a second server computing device that is in network communication with the computing device, wherein the server computing device executes a server supplement application, and further wherein the server supplement application is configured to generate search results based upon the context data;
   receiving the search results from the second server computing device; and
   responsive to receiving the search results, displaying the search results in a GUI of a client supplement application being executed by the at least one processor, wherein the GUI of the client supplement application is displayed on a display of the computing device concurrently with the GUI of the client EHR and beside the GUI of the client EHR.

2. The computing device of claim 1, wherein the client supplement application is configured to detect the API call generated by the client EHR application.

3. The computing device of claim 1, wherein the API call is an HTTP/s request, and wherein detecting the API call comprises monitoring a port for the HTTP/s request.

4. The computing device of claim 3, wherein the client supplement application, when executed by the at least one processor, monitors the port for the HTTP/s request, and wherein the GUI of the client supplement application is displayed in response to the client supplement application detecting the API call.

5. The computing device of claim 1, wherein the context data comprises an identifier for a patient, and further wherein the content presented in the GUI of the client EHR comprises medical information about the patient.

6. The computing device of claim 1, wherein the search results comprise population data, wherein the population data includes data about a patient population that includes the patient.

7. The computing device of claim 1, wherein the context data comprises an identifier for a healthcare worker that has provided authentication data to the client EHR.

8. The computing device of claim 1, wherein the at least one processor launches the client supplement application in response to detecting the API call.

9. The computing device of claim 1, wherein the client supplement application causes the computing device to transmit the context data to the second server computing device.

10. The computing device of claim 1, the acts further comprising:
detecting that a trigger has been activated by a healthcare worker that is operating the computing device; and
generating the API call in response to detecting that the trigger has been activated.

11. The computing device of claim 1, wherein the client EHR fails to support HL7 CCOW.

12. A method operated by a client computing device that executes a client electronic health record application (EHR) and a client supplement application, the method comprising:
detecting that the client EHR has output an API call to a server EHR that is executing on a first server computing device that is in network communication with the client computing device, the API call comprises context data, the context data indicative of content presented on a display of the client computing device in a graphical user interface (GUI) of the client EHR;
responsive to detecting that the client EHR has output the API call, extracting the context data from the API call and transmitting the context data in the API call to a second server computing device, wherein the second server computing device executes a server supplement application that is in communication with the client supplement application, and further wherein the server supplement application is configured to search over data maintained by the server supplement application and generate search results based upon the context data;
receiving the search results from the second server computing device; and
responsive to receiving the search results, displaying the search results in a GUI of the client supplement application, wherein the GUI of the client EHR is displayed beside the GUI of the client supplement application on the display.

13. The method of claim 12, wherein the API call is an HTTP/s request, and wherein detecting that the client EHR has output the API call comprises monitoring a port for the HTTP/s request.

14. The method of claim 13, wherein the client supplement application is configured to monitor the port for the HTTP/s request.

15. The method of claim 12, the acts further comprising:
responsive to detecting that the client EHR has output the API call, overlaying the GUI of the client supplement application on the GUI of the client EHR such that the GUI of the supplement application entirely covers the GUI of the client EHR, wherein a portion of the GUI of the supplement application is transparent such that a portion of the GUI of the client EHR remains visible on the display.

16. The method of claim 12, the acts further comprising:
responsive to detecting that the client EHR has output the API call, displaying the GUI of the client supplement application on the display;
detecting that a position of a cursor is outside of the GUI of the client supplement application; and
fading the GUI of the client supplement application out responsive to detecting that the position of the cursor is outside of the GUI of the client supplement application.

17. The method of claim 12, wherein the context data comprises an identifier of a patient, and further wherein the GUI of the client EHR depicts information about the patient.

18. The method of claim 17, wherein the search results comprise data about the patient obtained from a second server EHR.

19. The method of claim 12, wherein the GUI of the client supplement application includes a hyperlink, the method further comprising:
detecting that the hyperlink has been selected; and
responsive to detecting that the hyperlink has been selected, displaying a window over the GUI of the client EHR, the window comprises data that corresponds to the hyperlink.

20. A computer-readable storage medium comprising instructions that, when executed by at least one processor, cause the at least one processor to perform acts comprising:
detecting that a client electronic health record (EHR) application has output an HTTP/s request to a server EHR that is executing on a first server computing device, the HTTP/s request comprises context data, the context data comprises an identifier for a patient, wherein a GUI of the client EHR depicts information about the patient when the client EHR outputs the HTTP/s request;
responsive to detecting that the client EHR has output the HTTP/s request, extracting the context data from the API call and transmitting the context data to a second server computing device that executes a server supplement application, the server supplement application configured to search over patient population data based upon the context data and obtain search results from the patient population data;
receiving the search results from the second server computing device; and
responsive to receiving the search results, causing the search results to be displayed in a GUI of a client supplement application that is in communication with the server supplement application, wherein the GUI of the client supplement application is displayed beside the GUI of the client EHR.

* * * * *